United States Patent [19]
Lee et al.

[11] Patent Number: 5,976,888
[45] Date of Patent: Nov. 2, 1999

[54] METHOD FOR MEASURING $NO_x$ IN BIOCHEMICAL PROCESSES

[75] Inventors: Jaw Fang Lee, Berwyn; Sergey K. Maneshin, Upper Holland; Marcus E. Kolb, Phoenixville; Xin Yang, Holland, all of Pa.

[73] Assignee: BioChem Technology, Inc., King of Prussia, Pa.

[21] Appl. No.: 09/206,543

[22] Filed: Dec. 7, 1998

[51] Int. Cl.$^6$ .................................................. G01N 27/00
[52] U.S. Cl. .............................. 436/110; 436/55; 436/62; 436/106; 436/117; 436/118; 436/150; 210/96.1; 210/614; 422/79
[58] Field of Search ............................... 436/55, 62, 106, 436/110, 117, 118, 150; 210/96.1, 614; 422/79

[56] References Cited

U.S. PATENT DOCUMENTS

| | | | |
|---|---|---|---|
| 3,348,409 | 10/1967 | Arthur | 73/19 |
| 3,354,057 | 11/1967 | Klingelhoefer | 204/1 |
| 3,374,065 | 3/1968 | Suzuki | 23/253 |
| 3,565,583 | 2/1971 | McNulty et al. | 23/230 |
| 3,616,273 | 10/1971 | Oita | 240/1 T |
| 3,877,875 | 4/1975 | Jones et al. | 23/230 PT |
| 4,162,195 | 7/1979 | Solyom et al. | 43/310 |
| 4,209,299 | 6/1980 | Carlson | 23/230 R |
| 4,216,065 | 8/1980 | Rechnitz et al. | 240/1 T |
| 4,220,715 | 9/1980 | Ahnell | 435/34 |
| 4,277,343 | 7/1981 | Paz | 210/614 |
| 4,288,229 | 9/1981 | Mar | 23/230 PC |
| 4,297,173 | 10/1981 | Hikuma et al. | 204/1 T |
| 4,666,610 | 5/1987 | Kuhns | 210/749 |
| 4,845,025 | 7/1989 | Lary et al. | 435/2 |
| 5,013,442 | 5/1991 | Davis et al. | 210/614 |
| 5,389,524 | 2/1995 | Larsen et al. | 435/29 |
| 5,401,412 | 3/1995 | Yang et al. | 210/605 |
| 5,466,604 | 11/1995 | Yang et al. | 435/286.1 |
| 5,552,319 | 9/1996 | Yang et al. | 435/286.5 |
| 5,629,202 | 5/1997 | Su et al. | 435/286.5 |
| 5,641,966 | 6/1997 | Karlberg et al. | 258/373 |
| 5,658,802 | 8/1997 | Hayes et al. | 436/518 |
| 5,698,412 | 12/1997 | Lee et al. | 435/29 |
| 5,702,951 | 12/1997 | Bridger | 436/62 |
| 5,856,119 | 1/1999 | Lee et al. | 435/34 |

FOREIGN PATENT DOCUMENTS

| | | |
|---|---|---|
| 38 11 540 A1 | 10/1989 | Germany. |
| 59-99353 | 6/1984 | Japan. |

OTHER PUBLICATIONS

*Wat. Sci. Tech.* vol. 25, No. 6, pp. 43–57, 1992 Characterization Of Functional Microorganism Groups And Substrate In Activated Sludge And Wastewater By Aur, Nur And Our G. Holm Kristensen, P. Elberg Jørgensen and M. Henze.

Research Journal WPCF, Vol. 63, No. 3 Effects Of Oxygen Transport Limitation On Nitrification In The Activated Sludge Process Michael K. Stenstrom, Stephen S. Song.

Operations Forum, Feb. 1994 Alkalinity Tells All Real–Time Control For The Entire Process A.J. Freed, K.F. Davis.

*Toxicity Assessment: An International Journal*, vol. 4, 85–104 (1989) Anaerobic Subsurface Soil Microcosms: Methods to Monitor Effects of Organic Pollutants on Indigenous Microbial Activity Joel M. Dougherty and Guy R. Lanza.

*Wat. Sci. Tech.*, vol. 31, No. 7, pp. 181–189, 1995 Aerobic Biodegradation And Microbial Population Of A Synthetic Wastewater In A Channel With Suspended And Attached Biomass Y.S. Cao and G.J. Alaerts.

*Primary Examiner*—Jill Warden
*Assistant Examiner*—S. Carrillo
*Attorney, Agent, or Firm*—Schnader Harrison Segal & Lewis

[57] ABSTRACT

A method for measuring $NO_x$ in biochemical processes which includes a) isolating a liquid sample; b) adjusting the pH or ionic strength of the sample; c) recording mV values present in the sample after predetermined time periods; d) determining $NO_x$ concentrations in the sample at each of the predetermined time periods from the mV values; e) determining the difference in $NO_x$ in the sample from the $NO_x$ concentrations at each of the predetermined time periods; and f) determining the $NO_x$ concentration of the liquid sample from the difference in $NO_x$ and the predetermined time periods.

3 Claims, 10 Drawing Sheets

METHOD FOR MEASURING NO$_x$ IN BIOCHEMICAL PROCESSES

FIELD OF THE INVENTION

The present invention relates to apparatus and methods for measuring amounts of NO$_x$ (nitrate (NO$_3$) and/or nitrite (NO$_2$)) and nitrification/denitrification rates in liquid and controlling the treatment thereof, more particularly, to apparatus and methods for real time measuring the amount of NO$_x$ in liquids and nitrification/denitrification rates of liquids in a biochemical process and using the results of such measurement to control and/or adjust selected aspects of the process.

BACKGROUND OF THE INVENTION

The prior art has employed many devices and systems to process and purify water from industrial operations and municipal sources prior to discharging the water. Wastewater treatment plants (WWTP's), which are well known in the art, have been most often utilized to address this problem. Additionally, many industrial and municipal water treatment plants utilize biological systems to pre-treat their wastes prior to discharging into the usual municipal treatment plant.

Microorganisms used in the sludge break down or degrade contaminants for the desired water treatment in these processes. Efficient process performance and control requires quick and accurate assessment of information on the activity of the microorganisms. This has proven to be a difficult task in view of the wide variety of materials and contaminants that typically enter into treatment systems. Also, variations in the quantity of wastewater being treated, such as daily, weekly or seasonal changes, can dramatically change numerous important factors in the treatment process, such as pH, temperature, dissolved oxygen, nutrients and the like, alteration of which can be highly detrimental to proper wastewater treatment. Improperly treated wastewater poses serious human health dangers.

Various biological nutrient removal (BNR) processes are often used in biochemical systems/plants/processes. "BNR" is used hereinafter in a very generic sense, namely any biochemical process that uses microorganisms to remove nutrients. In BNR processes, contaminants in liquids such as wastewater, particularly carbon sources (measured as biochemical oxygen demand or BOD), ammonia, nitrates, phosphates and the like are digested by activated sludge in anaerobic, anoxic and aerobic (oxic) stages, also known in the art. In the anaerobic stage, wastewater, with or without passing through a preliminary settlement process, is mixed with return activated sludge (RAS), sometimes hereinafter referred to as "mixed liquor."

It is, of course, important to quantify the various contaminants in the wastewater. One of those contaminants that is important to quantify is the amount of NO$_x$. This is because quantification of the amount of NO$_x$ provides valuable information about nitrification and denitrification processes. Also, it is important to determine the nitrification or denitrification rate to facilitate adjustment of various system parameters, such as retention time, to enhance the treatment process and increase treatment system efficiency in response to this important information.

OBJECTS OF THE INVENTION

It is an object of the present invention to provide apparatus and a method for measuring the amount of NO$_x$ in biochemical systems to maximize the efficiency of the treatment process.

It is a further object of the present invention to provide apparatus and a method for measuring nitrification and/or denitrification rates to enhance control of biochemical processes, to maximize process performance in response to transient and other conditions.

Other objects of the present invention will be apparent to those of ordinary skill in the art based on the following drawings, detailed description of preferred embodiments and the appended claims.

SUMMARY OF THE INVENTION

One aspect of the invention includes a method of measuring the nitrification rate for a liquid including isolating a first liquid sample at $t_0$; recording a value of ammonia $[NH_3]_1$ present in the first sample at a predetermined time $t_1$; isolating a second liquid sample and introducing air into the second liquid sample after another predetermined time $t_2$; terminating the introduction of air into the second liquid sample and adjusting the pH of the second sample at $t_3$; recording another value of ammonia $[NH_3]_2$ in the second sample at a predetermined time $t_4$; and determining the nitrification rate of the liquid according to the following formula:

$$NR = \frac{\Delta[NH_3]}{\Delta t}$$

wherein NR is the nitrification rate, $\Delta t$ is $t_2$–$t_3$ and $\Delta[NH_3]$ is $[NH_3]_1$–$[NH_3]_2$.

Another aspect of the invention includes another method of measuring a nitrification rate for liquids including isolating first and second liquid samples and introducing air into the second liquid sample at $t_0$; recording a value of ammonia $[NH_3]_1$ present in the first sample and terminating introduction of air into the second sample at $t_1$; recording a value of ammonia $[NH_3]_2$ present in the second sample at $t_2$; and determining the nitrification rate of the liquid according to the following formula:

$$NR = \frac{\Delta[NH_3]}{\Delta t}$$

wherein NR is the nitrification rate, $\Delta t$ is $t_1$–$t_2$ and $\Delta[NH_3]$ is $[NH_3]_1$–$[NH_3]_2$.

The words "ammonia" ($[NH_3]$) and "ammonium" ($[NH_4^+]$) are hereafter often used interchangeably regarding the concentration of ammonia in the aqueous phase. This is because at a given pH, there exists a chemical equilibrium between ammonia molecules and ammonium ions in the aqueous phase. This equilibrium is described in the following form with the equilibrium constant equal to one, at pH=9.25.

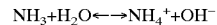

$$NH_3 + H_2O \leftrightarrow NH_4^+ + OH^-$$

The measurements of ammonia $[NH_3]$ and ammonium $[NH_4^+]$ are substantially equivalent so long as the pH value of the solution is known. It is advantageous to measure ammonium concentration, $[NH_4^+]$, at a lower pH (pH<6), while the measurement of ammonia concentration, $[NH_3]$, is more convenient at an elevated pH (pH>8). The discussion of this invention often refers to the ammonia concentration as $[NH_3]$ measured with an ammonia selective probe, with the understanding that at a lower pH, it can be replaced by $[NH_4^+]$ measured with an ammonium ion selective probe.

The invention also includes a method of measuring NO$_x$ in liquids, especially wastewater. This method is different from other analyzing methods in that there is no need to prepare the sample by filtration or other method of solids removal. The method includes isolating a wastewater sample; adjusting the pH and/or ionic strength of the sample to a predetermined level for a predetermined time interval $t_1$; recording a value of $[NO_x]_1$ present in the sample with an $NO_x$ selective probe(s); recording another value of $[NO_x]_2$ present in the sample after another predetermined time interval $t_2$; determining $NO_x$ concentrations in the sample at each predetermined time interval $t_1$ and $t_2$ according to the following formula:

$$[NO_x] = 10^{a \cdot mV + b}$$

wherein a and b are linear coefficients of the $NO_x$ probe and mV reading is from the $NO_x$ ion selective probe(s); determining the changes in $NO_x$ according to the following formula:

$$\Delta[NO_x] = [NO_x]_2 - [NO_x]_1;$$

and determining the $NO_x$ concentration of the sample according to the following formula:

$$[NO_x] = [NO_x]_1 - \frac{\Delta[NO_x]}{\Delta t} \cdot t_1.$$

In yet another aspect of the invention, the rate of denitrification may be determined. The denitrification rate (DR) may be determined as follows: isolating a liquid sample at $t_0$; recording a value of $[NO_x]_1$ present in the sample at a predetermined time $t_1$; recording a value of $[NO_x]_2$ present in the sample at a predetermined time $t_2$; and determining the denitrification rate of the liquid according to the following formula:

$$DR = \frac{\Delta[NO_x]}{\Delta t},$$

wherein $\Delta[NO_x]$ is $[NO_x]_1 - [NO_x]_2$ and $\Delta t = t_2 - t_1$.

DETAILED DESCRIPTION OF THE INVENTION

Figure 1:
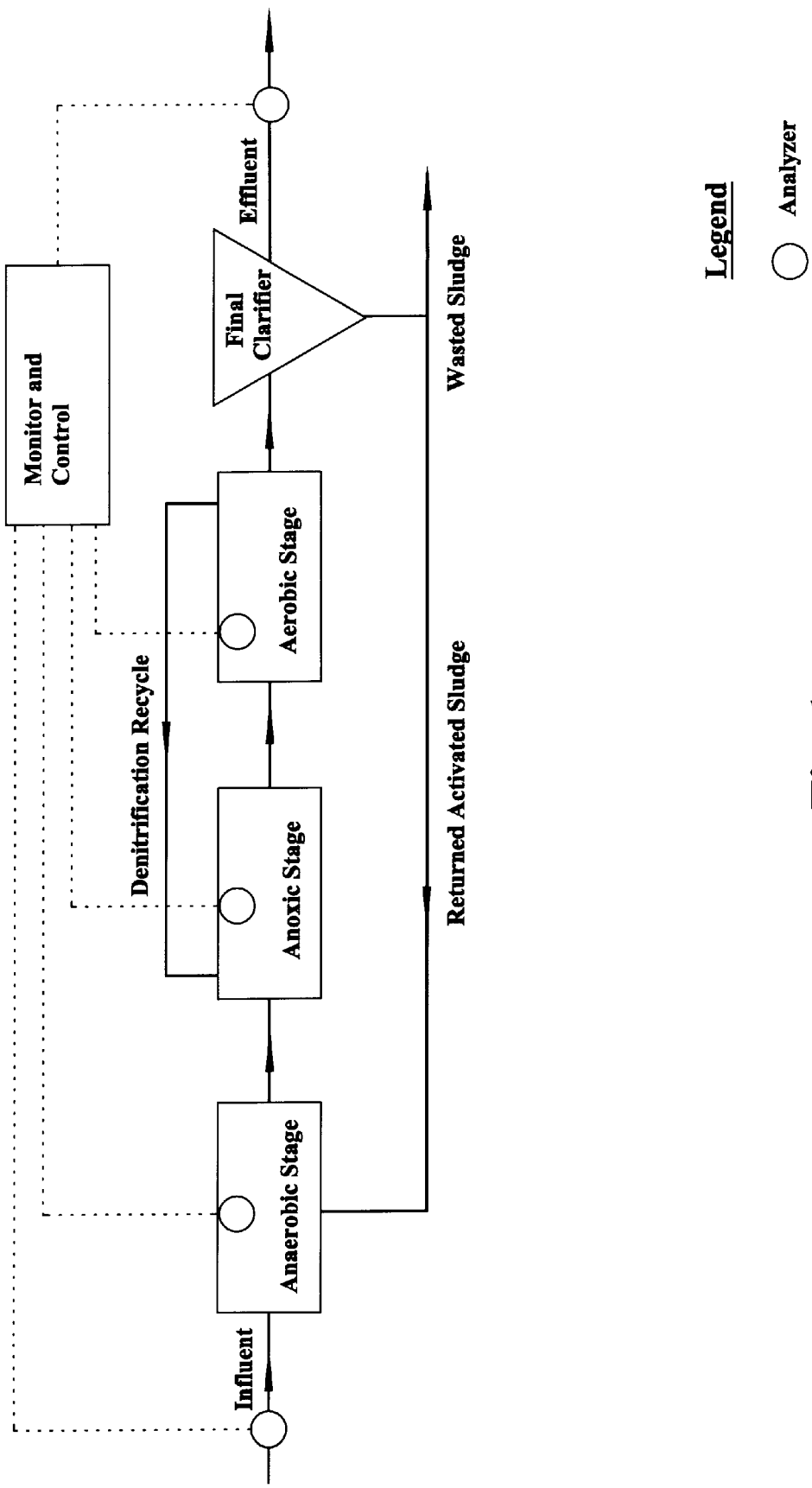
FIG. 1 is a schematic of a typical wastewater treatment process utilizing embodiments of the invention and shows the many locations that detectors can be installed through out the system.

The following description is intended to refer to specific embodiments of the invention illustrated in the drawings and is not intended to define or limit the invention, other than in the appended claims. Also, the drawings are not to scale and various dimensions and proportions are contemplated.

In order to effectively control the operation of the BNR process, it is necessary to regulate specific process parameters based upon the biological activity of the microorganisms in the anaerobic, anoxic and/or oxic stages of the treatment. Wastewater treatment plants are often subjected to severe transient conditions, such as diurnal variations in organic loads.

The proper evaluation and control of a BNR process requires an accurate and current assessment of the amount of $NO_x$ and ammonia in the mixed liquor, the nitrification rate and the denitrification rate, among other things, in a variety of environments and under a number of conditions.

The apparatus for quantifying ammonia and/or $NO_x$ and/or nitrification rate and/or denitrification rate can be used in all stages of a WWTP or any combination thereof. Incorporation of the apparatus into a typical WWTP is shown schematically in FIG. 1. $NO_x$ and/or ammonia measurements may be taken at any point or location in the system shown in FIG. 1. This includes multiple measurement locations within a selected stage, if desired. The general application and use of the apparatus in the anaerobic, anoxic and/or aerobic stages of a typical wastewater treatment plant will now be discussed.

Figure 2:
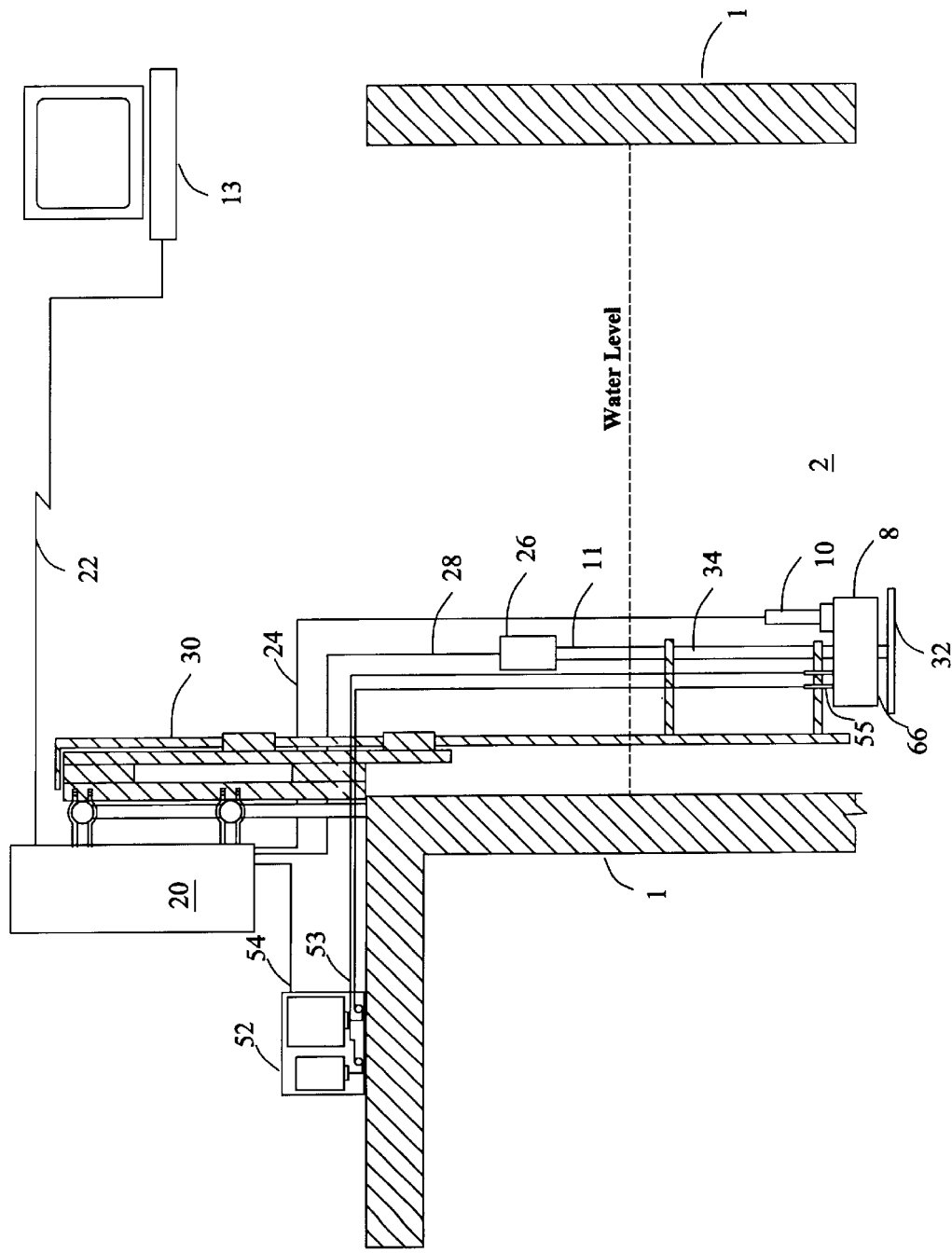
FIG. 2 shows a schematic front elevational view of an embodiment of apparatus of the invention used to monitor a bioreactor tank.

One embodiment of apparatus for sampling wastewater is shown in FIG. 2. A bioreactor tank 1 (or, alternatively, a wastewater channel) contains wastewater 2 and/or sludge. Detection apparatus is mounted on the top of bioreactor tank 1 and extends into wastewater 2. The apparatus includes a central control and analysis unit 20 connected to optional computer/monitor 13 by wire or wireless connection 22. Similarly, central control and analysis unit 20 connects to detection probe 10 by way of wire connection 24. Motor container 26 also connects to central control and analysis unit 20 by way of connection wire 28. Power is supplied to motor container 26 also by wire connection 28.

Detection probe 10 is positioned in detection chamber 8 and electrically connected to central control and analysis unit 20 to detect changes in the quantity of ammonia or ammonium or $NO_x$ concentration in wastewater samples depending on the configuration. At low pH, a preferred ammonium ion selective probe 10 is an ammonium probe manufactured by HACH or NICO. At mid-high pH a preferred ammonia detection probe 10 is an ammonia gas probe also manufactured by NICO or HACH. A preferred $NO_3$ and/or $NO_2$ ion selective probe(s) are manufactured by NICO. Of course, other apparatus can be employed as probes so long as the same or similar detection capabilities are available.

Optional computer/monitor 13 may be of any suitable type such as a personal computer or the like. Device 52 consists of two containers (one storing ammonia or $NO_x$ calibration solution and the other storing pH adjustment solution and/or ionic strength adjustment solution) and a delivery device for each, for example, a pump. Device 52 is connected to central control and analysis unit 20 by wire 54. Device 52 provides ammonia or $NO_x$ calibration and pH adjustment solution and/or ionic strength adjustment solution to the liquid (e.g. wastewater) in detection chamber 8 by connection tube 53 through feed ports 55. The pH adjustment solution, typically a base for mid to high pH and an acid for low pH, may be selected from a wide variety of pH altering solutions. Bases include NaOH, KOH and the like. Acids include HCl, acetic acid and the like. The ionic strength adjustment solution, typically $Al_2(SO_4)_3$ solution, or solution of $Al_2(SO_4)_3$, $Ag_2SO_4$, $H_3BO_3$, and sulfamic acid, can be selected from a wide variety of solutions for the adjustment of ionic strength of the wastewater sample. Device 52 is described in detail below in conjunction with FIG. 6.

Sampling unit 11 is mounted onto a movable carriage 30 which is capable of moving substantially vertically upwardly and downwardly to move sampling unit 11 into and out of wastewater 2. The precise structure of movable carriage 30 is not critical so long as the preferred capability or movability of sampling unit 11 is achieved.

Detection probe 10 has its detection end located in detection chamber 8. Detection chamber 8 has an opening 66 and an adjacent movable cover 32 which moves vertically upwardly and downwardly along guide channels 34 and closes or seals opening 66.

Figure 3:
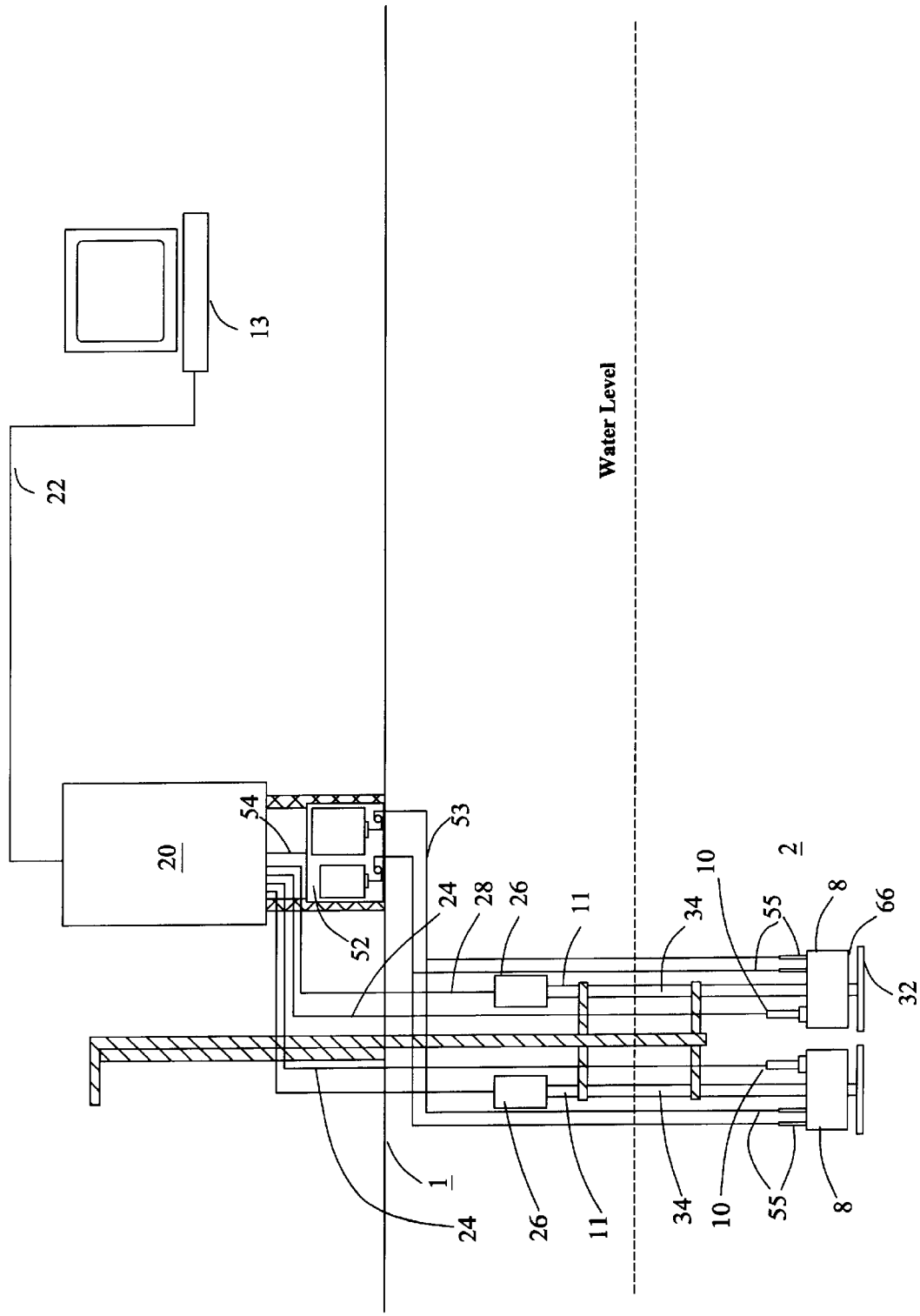
FIG. 3 shows a schematic front elevational view of another embodiment of apparatus of the invention used to monitor a bioreactor tank.

FIG. 3 shows another embodiment of apparatus for sampling wastewater. The embodiment shown in FIG. 3 is similar to that shown in FIG. 2 except that apparatus providing for additional sampling capability is provided. Specifically, another detection chamber 8 having a probe 10 is mounted adjacent to the detection chamber/probe configuration shown in FIG. 2. Of course, additional connections are provided to the control and analysis unit 20 and solution supplied by device 52.

Figure 4:
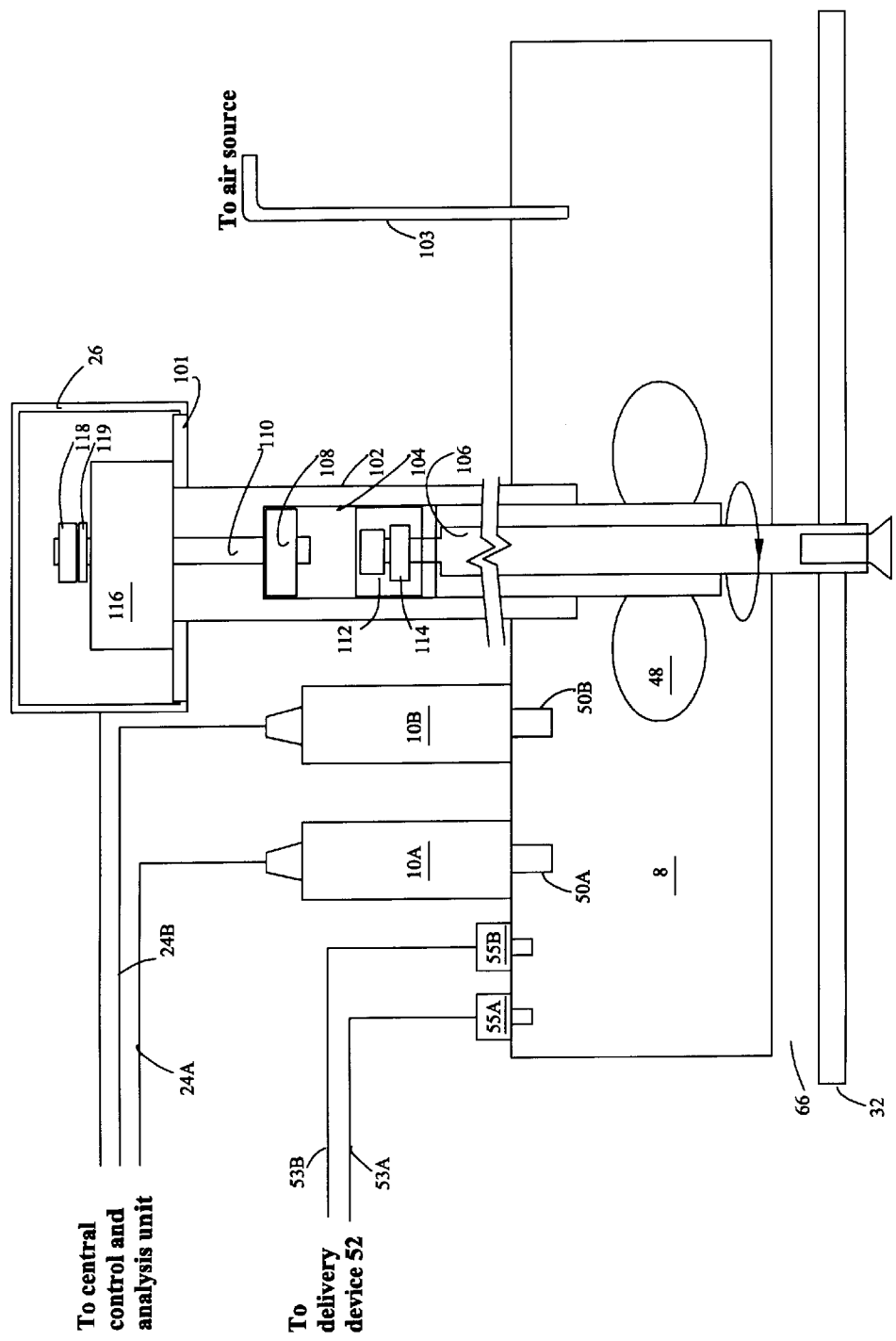
FIG. 4 shows an exploded schematic view, partially taken in section, of wastewater sampling apparatus in accordance with aspects of the invention.

FIG. 4 shows detection chamber 8 having a detection probe 10A with a detection end 50A. Detection probe 10A may be an ammonia, ammonium or an $NO_x$ detection probe. Detection chamber 8 also has an optional detection probe 10B with a detection end 50B. Optional detection probe 10B is a pH probe. Detection chamber 8 still further has feed ports 55A and 55B. Feed device 52 feeds pH adjustment solution and/or ionic strength adjustment solution into detection chamber 8 through feed port 55B. Feed device 52 feeds ammonia or $NO_x$ to detection chamber 8 through feed port 55A. Propeller 48 is located interiorly of detection chamber 8 and stirs or agitates samples when probes 10A and 10B are in operation. Cover 32 is in an open position which, when closed, covers opening 66.

Propeller 48 is connected to motor container 26 by way of a series of coaxial tubes 102, 104 and 106. An adaptor 108 and a thrust bearing sleeve 112 are contained in and attached to middle tube 104. Outside tube 102 is mounted to base 101. Adaptor 108 is attached to threaded rod 110 to either open or close cover 32 depending on motor direction of linear actuator motor 116. Middle tube 104 travels axially only if induced drag on middle tube 104 exceeds an amount of torque required for linear actuator motor 116 to turn on threaded rod 110. This drag can be induced by propeller 48 attached to middle tube 104 and/or any bushings or other hardware in contact with middle tube 104. Thrust bearing sleeve 112 holds bearing 114 which carries axial tension of central tube 106 when cover 32 is closed. Bearing 114 allows middle tube 104 to rotate independently of central tube 106 and transfers axial motion of tube 104 to central tube 106. Outside tube 102 supports both base 101 and chamber 8 while protecting the internal parts.

Chamber 8 is substantially sealed to outside tube 102 and when cover 32 is pulled against chamber 8 the space inside chamber 8 is sealed.

When linear actuator motor 116 rotates in one direction threaded rod 110 travels downward, pushing cover 32 open. When nut 118 reaches thrust bearing 119, threaded rod 110 no longer travels axially and this causes middle tube 104 to substantially match the motor speed. Chamber 8 is then in an open condition and propeller 48 induces an exchange of fluid between the inside and outside of chamber 8.

When linear actuator motor 116 rotates in the opposite direction, threaded rod 110 travels upward, pulling cover 32 closed. When chamber 8 is closed, axial motion of threaded rod 110 is prevented by tension on middle tube 104. This causes middle tube 104 to rotate at the same speed as motor 116. Chamber 8 is then in a closed position so that fluid is retained inside chamber 8 while being constantly mixed by propeller 48.

Figure 5:
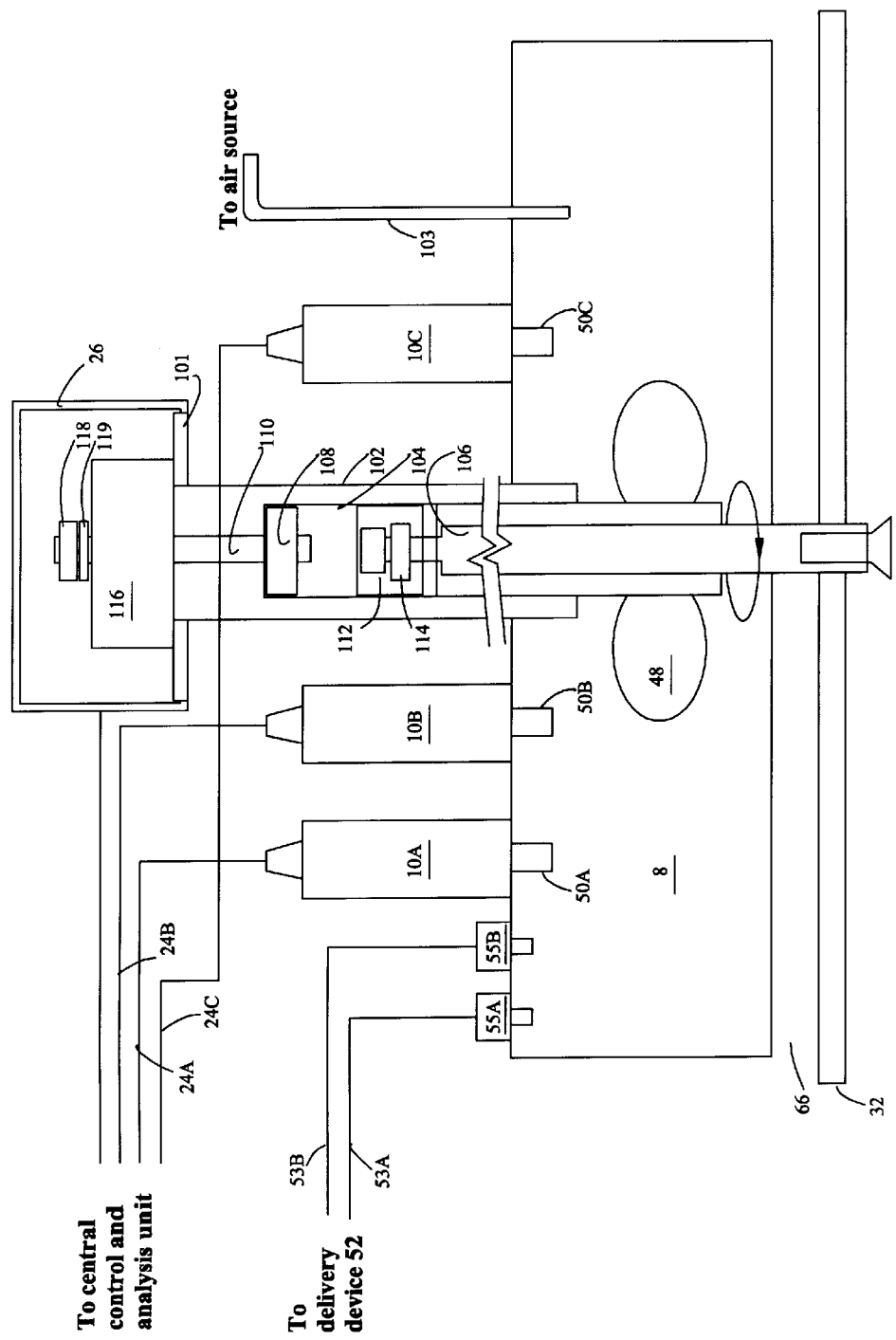
FIG. 5 shows an exploded schematic view, partially taken in section, of wastewater sampling apparatus in accordance with another embodiment of the invention.

FIG. 5 shows another embodiment of a chamber 8 configuration containing an optional additional detection probe. All other components are the same as shown in FIG. 4. Optional detection probe 10C has a detection end 50. Optional detection probe 10C is a dissolved oxygen probe. It connects to central control and analysis unit 20 by way of connection 24C.

Figure 6:
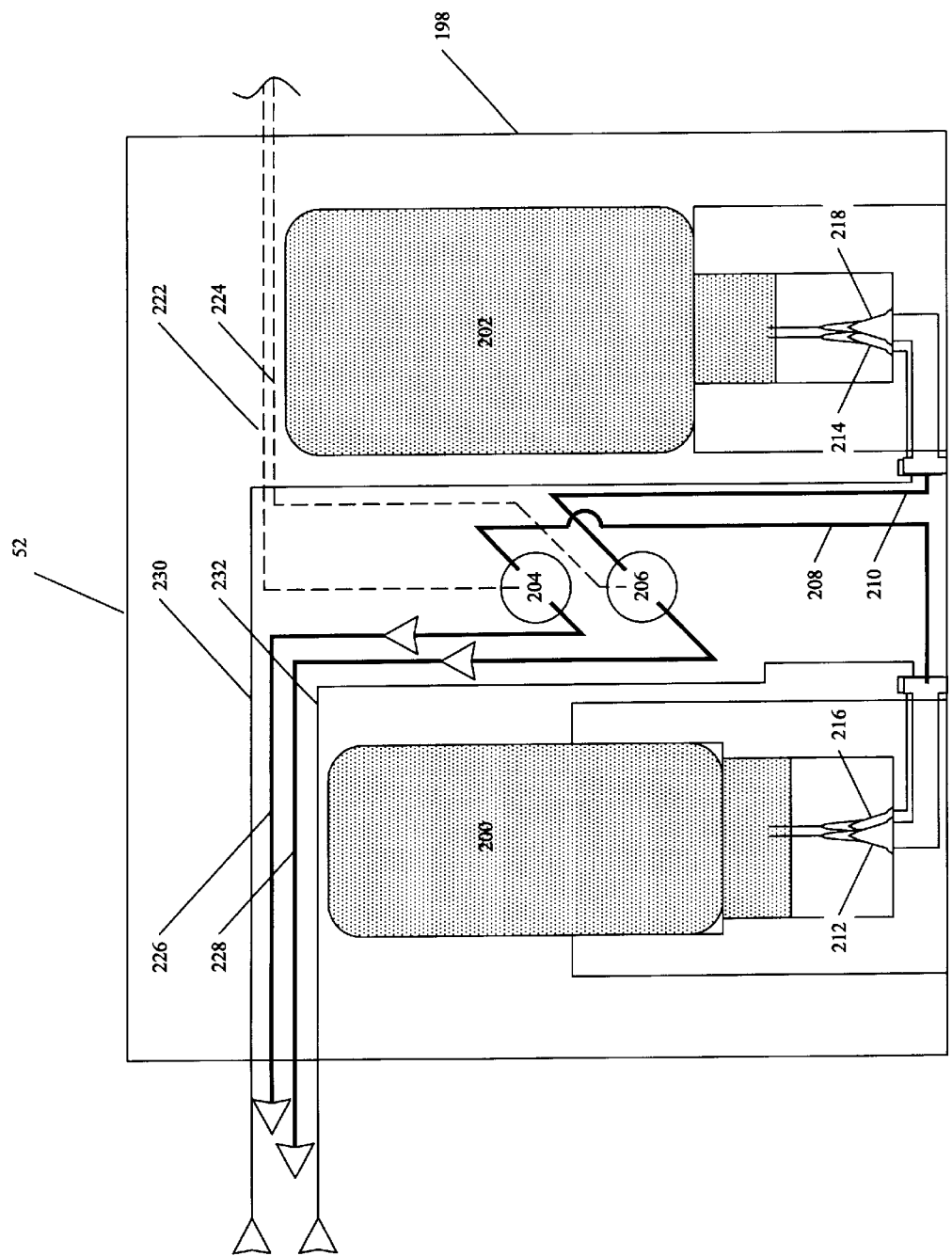
FIG. 6 shows a schematic view, partially taken in section, of solution dispenser apparatus in accordance with aspects of the invention.

Referring to FIG. 6, device 52 is constructed to accurately dispense various solutions to other components of the overall system. Device 52 includes a housing 198 and preferably contains two solution containers 200 and 202, although it may be configured to contain only one or more than two solution containers. The containers 200 and 202 have corresponding solution pumps 204 and 206 connected to their respective solution containers with pump feeding lines 208 and 210. The pump feeding lines are preferably equipped with a sharp or needle-type device 212 and 214 that extend though housing 198.

Each solution container is preferably made of a plastic material that is pierceable by the needle or sharp device, whereby when the solution container is lowered onto the needle, it punctures the container to provide access to the solution. Most preferably, the container is shaped to urge liquid in the solution container to flow towards the needle device.

Since it is important that the solutions remain uncontaminated and retain their precise concentration, for measurement purposes, it is important that they are sealed. However, in emptying the container, it is highly preferred to provide a means for air to fill in the space created in the container when solution is removed. This may be achieved by a number of means, although it is highly preferred to use needle-type device 216 and 218 to puncture solution containers 200 and 202 and provide air access to the interior of the solution containers. The needle-type device 216 and 218 are connected to air lines 230 and 232.

Each pump 204 and 206 connected to the respective solution containers connects control and analysis unit 20 (not shown in FIG. 6), by line 222 and 224. The pumps 204 and 206 also connect to detection chamber(s) 8 (not shown in FIG. 6), by way of solution feeding lines 226 and 228 to supply the metered or precise quantity of solution to detection chamber(s) 8 at the specific time.

Of course, the solution within the containers may vary. However, the preferred solution(s) are ammonium chloride or sodium nitrate. The pH and/or ionic strength adjustment solution(s) also can also be held in the containers. Other solutions may be utilized in accordance with the particular need. Solutions may, of course, be in various concentrations as needed.

$NO_x$ is often a main part of the contaminants in wastewater. Therefore, a fast and easy method for real-time measurement of $NO_x$ in wastewater is highly advantageous. Accordingly, one aspect of the invention involves measuring the amount of $NO_x$ in the wastewater. This is performed by a method of measuring $NO_x$ in liquid including isolating a liquid sample; adjusting the pH and/or ionic strength of the sample at time $t_0$; recording a value of $NO_x$ present in the sample with an $NO_x$ selective probe(s) at a predetermined time $t_1$; recording another value of $NO_x$ present in the sample after another predetermined time $t_2$; determining $NO_x$ concentrations in the sample at each predetermined time $t_1$ and $t_2$ according to the following formula:

$$[NO_x] = 10^{a \cdot mV + b}$$

wherein a and b are linear coefficients of the $NO_x$ probe(s); determining the change in $NO_x$ in the sample according to the following formula:

$$\Delta[NO_x] = [NO_x]_2 - [NO_x]_1;$$

and determining the $NO_x$ concentration of the sample according to the following formula:

$$[NO_x]_0 = [NO_x]_1 - \frac{\Delta[NO_x]}{\Delta t} \cdot (t_1 - t_0).$$

Figure 7:
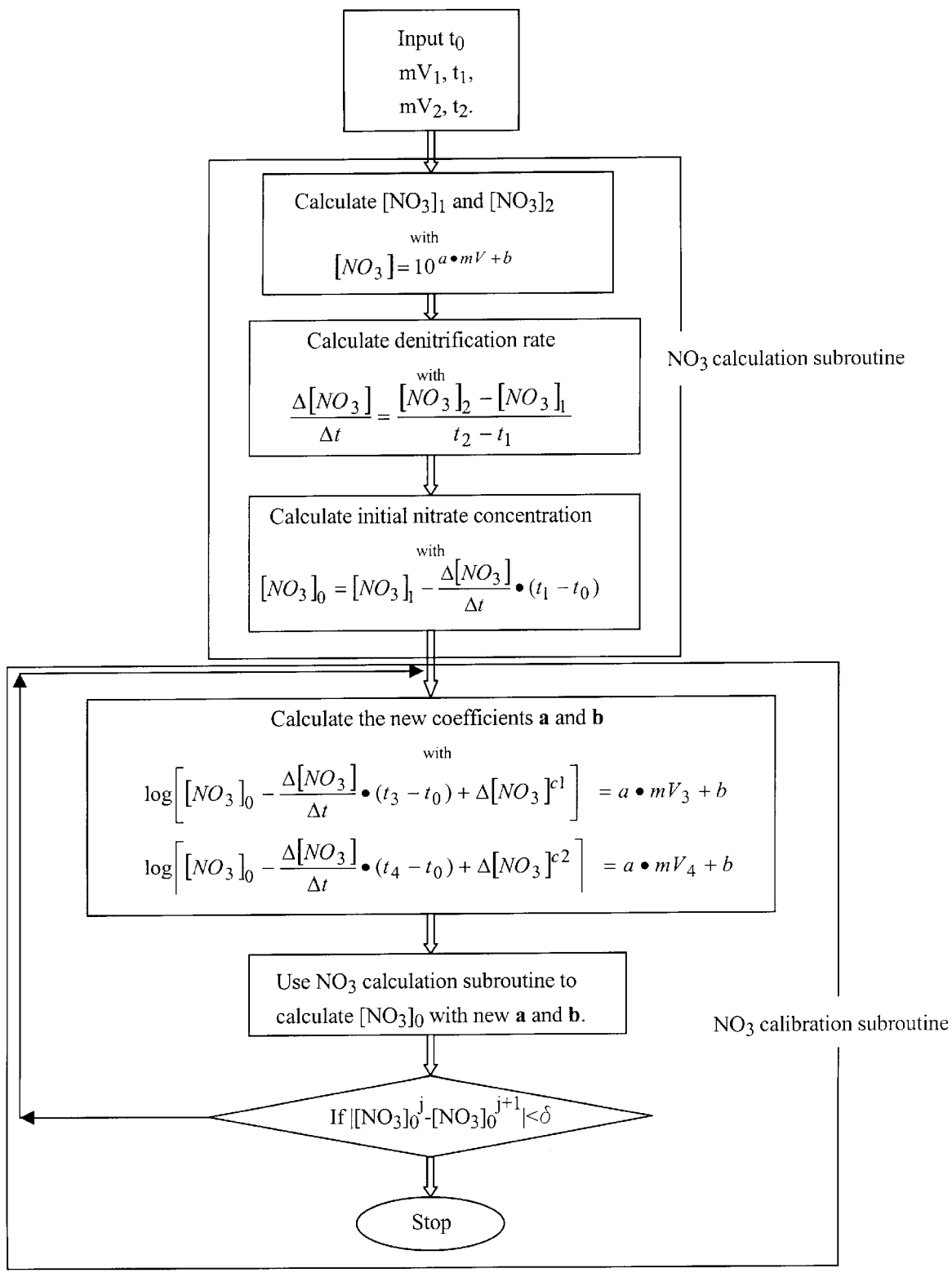
FIG. 7 is a block diagram of a method to measure $NO_x$ and a method of calibrating an $NO_x$ analyzer in accordance with aspects of the invention.

This method is shown in the upper portion of the flow diagram shown in FIG. 7.

The $NO_x$ analyzer can be calibrated according to the lower portion of the block diagram shown in FIG. 7 and according to the following method:

a) Collect a mixed liquor sample from the wastewater treatment tank and conduct $NO_x$ analysis as described above, except that the sample is not discharged to the treatment tank after the $NO_x$ concentration is measured. Parameters and intermediate results such as $[NO_x]_1$, $[NO_x]_2$, $mV_1$, $mV_2$, $\Delta[NO_x]/\Delta t$ are saved for use in the calibration step.

b) After the $NO_x$ concentration is measured, a predetermined volume of nitrate or nitrite solution is injected into the sample container so that the concentration of $NO_x$ in the container increases by a $\Delta[NO_x]^{c1}$, (e.g. 0.5 ml of 1000 ppm $NaNO_3$ or $NaNO_2$ solution for $\Delta[NO_x]^{c1}=1$ ppm, assuming the sampling chamber has a volume of 500 ml.)

c) Wait to $t_3$ seconds to read the third mV reading from the probe $[mV_3]$.

d) Inject a second dose of calibration solution so that the concentration of $NO_x$ increases by a $\Delta[NO_x]^{c2}$, (e.g. 2.0 ml of 1000 ppm $NaNO_3$ or $NaNO_2$ solution for $\Delta[NO_x]^{c2}=5$ ppm, taken into account of the first dose of calibration solution.)

e) Wait to $t_4$ seconds to read the fourth mV reading from the probe $[mV_4]$.

f) Use the following equations to calculate the linear coefficients of $NO_x$, a and b:

$$\log[NO_x]_0 - \frac{\Delta[NO_x]}{\Delta t} \cdot (t_3 - t_0) + \Delta[NO_x]^{c1} = a \cdot mV_3 + b$$

$$\log[NO_x]_0 - \frac{\Delta[NO_x]}{\Delta t} \cdot (t_4 - t_0) + \Delta[NO_x]^{c2} = a \cdot mV_4 + b$$

g) Use the newly obtained a and b to calculate $[NO_x]_0$ from $mV_0$. If the newly calculated $[NO_x]_0$ substantially agrees with original $[NO_x]_0$, then the calibration is deemed successful, otherwise, use the newly calculated $[NO_x]_0$ to repeat the calibration process. The calibration is considered complete when the difference between $[NO_x]_0^j$ and $[NO_x]_0^{j+1}$ is within an acceptable, predetermined range.

h) Discharge the sample to the treatment tank and start a new measurement cycle.

i) The calibration of the $NO_x$ analyzer can be performed as frequently as every measurement cycle, or everyday. The default calibration frequency is preferably once a day.

It is still further advantageous to determine the nitrification rate. There are two preferred methods to make such a determination in accordance with the invention. In a first embodiment, the method includes:

a) isolating a first liquid sample at $t_0$;

b) measuring the concentration of ammonia $[NH_3]_1$ or ammonium $[NH_4^+]_1$ present in the sample at a predetermined time $t_1$, then releasing the first sample to the treatment tank;

c) isolating a second liquid sample and introducing air into the second liquid sample after another predetermined time $t_2$;

d) terminating the introduction of air into the second liquid sample and adjusting the pH of the second sample at $t_3$;

e) recording another value of ammonia $[NH_3]_2$ or ammonium $[NH_4^+]_2$ in the second sample at a predetermined time $t_4$; and f) determining the nitrification rate of the liquid according to the following formula:

$$NR = \frac{\Delta[NH_3]}{\Delta t} \text{ or } NR = \frac{\Delta[NH_4^+]}{\Delta t}$$

wherein NR is the nitrification rate, $\Delta t$ is $t_3 - t_2$ and $\Delta[NH_3]$ is $[NH_3]_1 - [NH_3]_2$ or $\Delta[NH_4^+]$ is $[NH_4^+]_1 - [NH_4^+]_2$.

Figure 10:
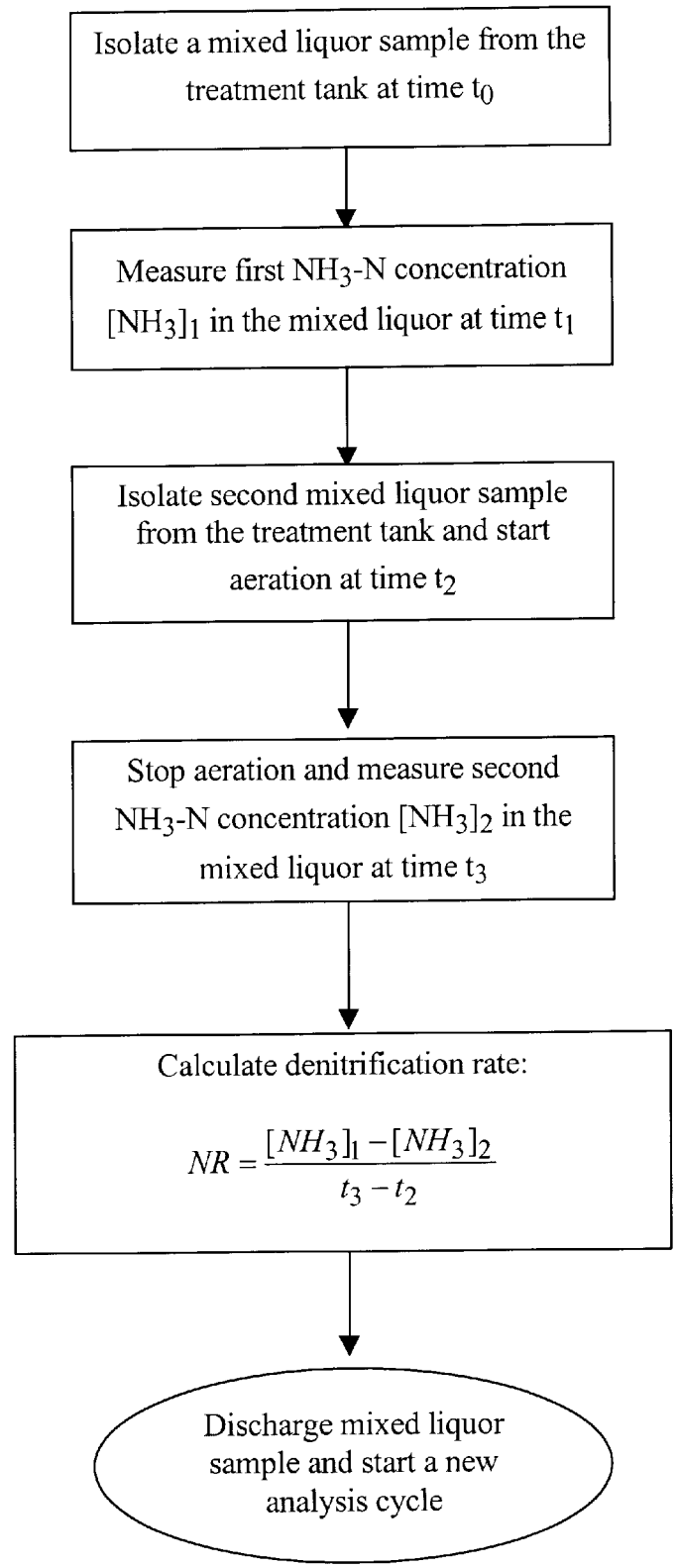
FIG. 10 is a block diagram of another method of determining the rate of nitrification of wastewater.

This method is outlined in the flow diagram shown in FIG. 10.

In the second embodiment which uses two sampling units (as shown in FIG. 3), the method includes:

a) isolating first and second liquid samples and introducing air into the second liquid sample at $t_0$;

b) measuring the concentration of ammonia $[NH_3]_1$ or ammonium $[NH_4^+]$ present in the first sample;

c) terminating introduction of air into the second sample at $t_1$;

d) measuring the concentration of ammonia $[NH_3]_2$ present in the second sample; and e) determining the nitrification rate of the liquid according to the following formula:

$$NR = \frac{\Delta[NH_3]}{\Delta t} \text{ or } NR = \frac{\Delta[NH_4^+]}{\Delta t}$$

wherein NR is the nitrification rate, $\Delta t$ is $t_1 - t_0$ and $\Delta[NH_3]$ is $[NH_3]_1 - [NH_3]_2$ or $\Delta[NH_4^+]$ is $[NH_4^+]_1 - [NH_4^+]_2$.

The preferred operation of the ammonia analyzer in the measurement mode is as follows:

a) Collect a mixed liquor sample from the wastewater treatment tank.

b) Inject pH adjustment solution to bring the pH of the water phase to about 12.0. This can be done either through a predetermined amount or feedback control by way of a pH probe. This is recorded as time zero, $t_0$.

c) Wait to $t_1$ seconds to read the first $mV_1$ reading from the ammonia probe.

d) Wait to $t_2$ seconds to read the second $mV_2$ reading from the ammonia probe.

e) Use the following equation to calculate ammonia concentrations from $mV_1$ and $mV_2$, where a and b are linear coefficients of the ammonia probe.

$$[NH_3] = 10^{a \cdot mV + b}$$

f) The amount of released $NH_3$ from the sample is calculated as:

$$\frac{\Delta[NH_3]}{\Delta t} = \frac{[NH_3]_2 - [NH_3]_1}{t_2 - t_1}$$

g) The ammonia concentration of the sample is calculated as:

$$[NH_3]_0 = [NH_3]_1 - \frac{\Delta[NH_3]}{\Delta t} \cdot (t_1 - t_0)$$

h) After the measurement of ammonia concentration, the sample is discharged to the treatment tank, and a fresh sample is taken for the next analysis.

The ammonia analyzer is preferably calibrated according to the following method:

a) Collect a mixed liquor sample from the wastewater treatment tank and conduct ammonia analysis as described above, except that the sample is not discharged to the treatment tank after the ammonia concentration is measured. Parameters and intermediate results such as $[NH_3]_1$, $[NH_3]_2$, $mV_1$, $mV_2$, $\Delta[NH_3]/\Delta t$ are saved for use in the calibration step. p1 b) After the ammonia concentration is measured, a predetermined volume of ammonia solution is injected into the sample container so that the concentration of ammonia in the container increases by a $\Delta[NH_3]^{c1}$, (e.g. 0.5 ml of 1000 ppm $NH_4Cl$—N solution for $\Delta[NH_3]^{c1}=1$ ppm, assuming the sampling chamber has a volume of 500 ml.)

c) Wait to $t_3$ seconds to read the third mV reading from the probe ($mV_3$).

d) Inject a second dose of calibration solution so that the concentration of ammonia increases by a $\Delta[NH_3]^{c2}$, (e.g. 2.0 ml of 1000 ppm $NH_4Cl$—N solution for $\Delta[NH_3]^{c2}=5$ ppm, taken into account of the first dose of calibration solution.)

e) Wait to $t_4$ seconds to read the fourth mV reading from the probe ($mV_4$).

f) Use the following equations to calculate the linear coefficients of ammonia, a and b:

$$\log[NH_3]_0 + \frac{\Delta[NH_3]}{\Delta t} \cdot (t_3 - t_0) + \Delta[NH_3]^{c1} = a \cdot mV_3 + b$$

$$\log[NH_3]_0 + \frac{\Delta[NH_3]}{\Delta t} \cdot (t_4 - t_0) + \Delta[NH_3]^{c2} = a \cdot mV_4 + b$$

g) Use the newly obtained a and b to calculate $[NH_3]_0$ from $mV_0$. If the newly calculated $[NH_3]_0$ substantially agrees with original $[NH_3]_0$, then the calibration is deemed successful, otherwise, use the newly calculated $[NH_3]_0$ to repeat the calibration process. The calibration is considered complete when the difference between $[NH_3]_0^j$ and $[NH_3]_0^{j+1}$ is within an acceptable, predetermined range.

h) Discharge the sample to the treatment tank and start a new measurement cycle.

The calibration of the ammonia analyzer can be performed as frequently as every measurement cycle, or everyday. The default calibration frequency is preferably once a day.

Figure 8:
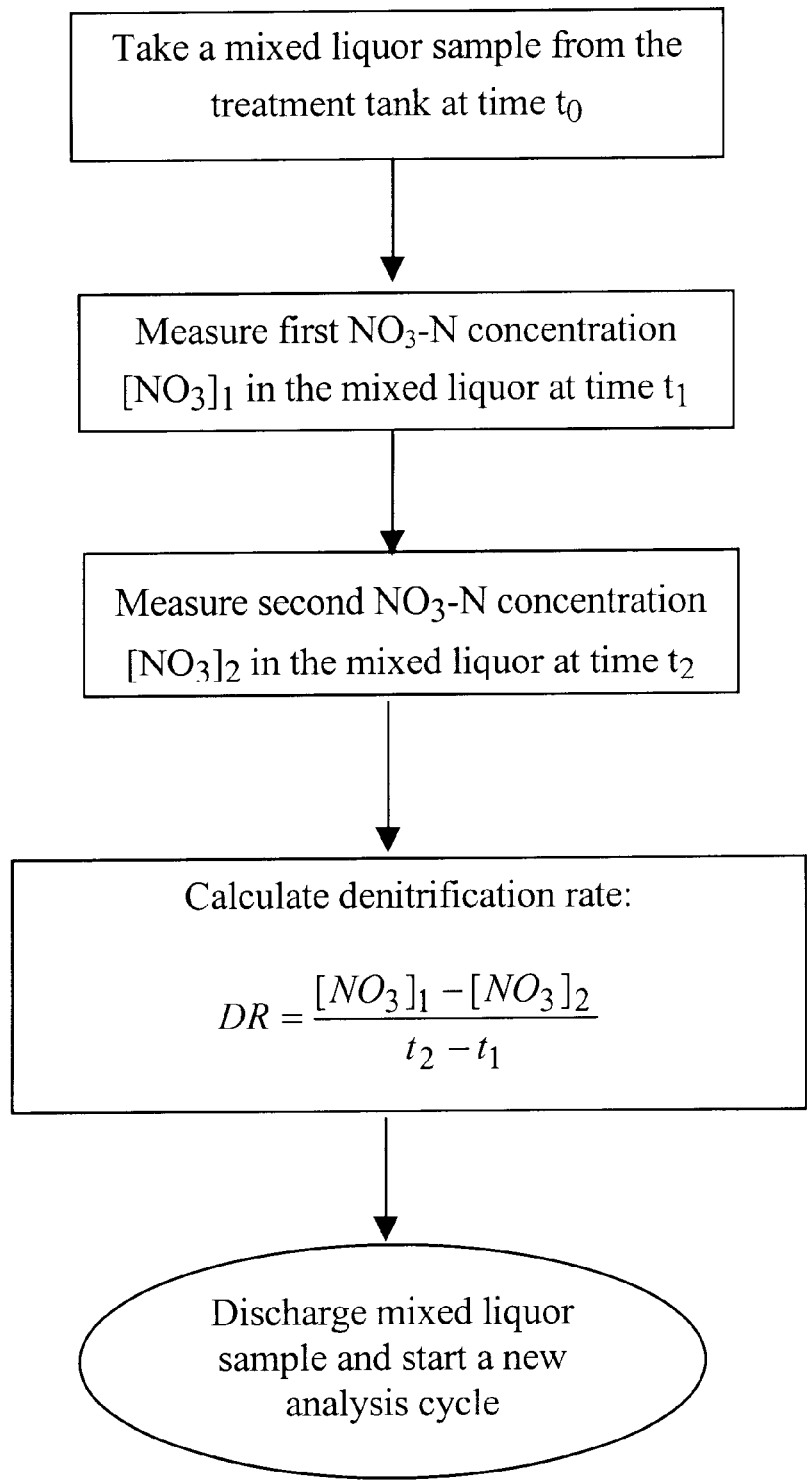
FIG. 8 is a block diagram of a method of determining the rate of denitrification of wastewater.
Figure 9:
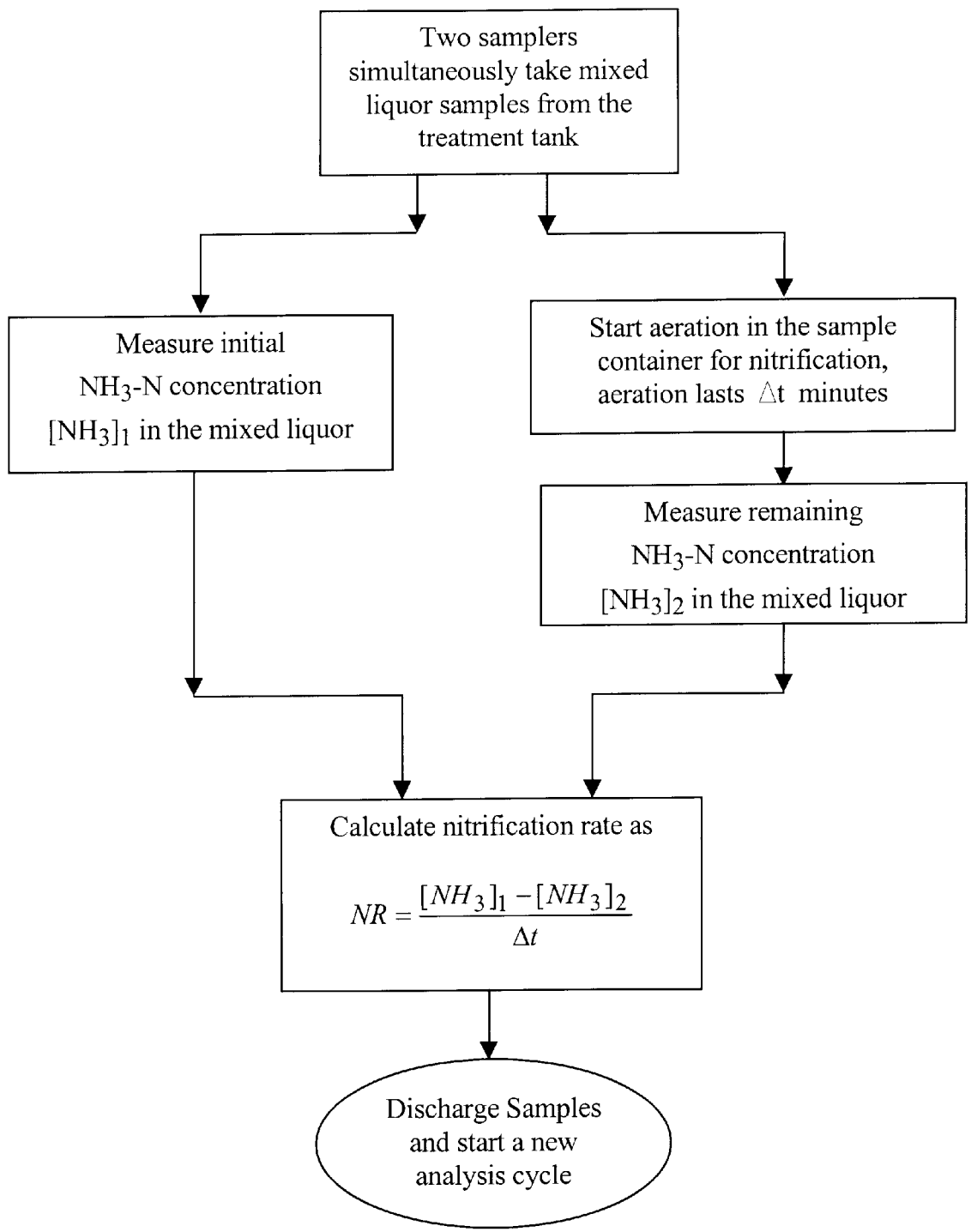
FIG. 9 is a block diagram of a method of determining the rate of nitrification of wastewater.

It is also advantageous to determine the denitrification rate (DR). Determination of DR depends on the concentrations of $NO_x$. It is calculated according to the method shown in the flow diagram of FIG. 8. The method includes:

a) isolating a liquid sample at $t_0$;

b) measuring the concentration of $NO_x$ ($[NO_x]_1$) present in the sample at a predetermined time $t_1$;

c) measuring the concentration of $NO_x$ ($[NO_x]_2$) present in the sample at a predetermined time $t_2$; and d) determining the denitrification rate of the liquid according to the following formula:

$$DR = \frac{\Delta[NO_x]}{\Delta t},$$

wherein $\Delta[NO_x]$ is $[NO_x]_1 - [NO_x]_2$ and $\Delta t = t_2 - t_1$.

One practical application of determining nitrification rate NR in the monitoring and control of wastewater treatment process is to evaluate and optimize the bioreactor's operation. When NR is measured on a real time basis, the information will answer the following:

1) Whether the activated sludge has nitrification ability, i.e. the presence of nitrification bacteria in the biomass. A low or near zero NR value indicates that the nitrifier population in the biomass is low or does not exist, whereas a high value of NR indicates a proper nitrification process.

2) Under the current wastewater loading to the plant, to what degree has nitrification been achieved? When NR is determined, the required time for proper ammonia removal can be calculated based on the nutrient loading. This required nitrification time can be compared with the current hydraulic retention time in the bioreactor to see if proper nitrification can be achieved.

3) What is the best aeration rate to achieve the desired degree of nitrification? The optimal air supply rate can be reached when the air supply calculated from the NR value matches the true air demand in the nitrification process. Over-aeration will result in deterioration of biomass and wasted energy, while under aeration may cause improper treatment of the wastewater. Both cases can be avoided with proper aeration control with NR as one of control parameters.

4) What is the best mean cell residence time (MCRT) of the biomass in the bioreactor for the desired degree of nitrification? The population of nitrification bacteria can be estimated from the NR value. This estimation allows the operator to determine the proper mean cell residence time (MCRT) for the desired growth of nitrification bacteria in the biomass. The MCRT may be used to control the wasting of the activated sludge.

5) What level of biomass concentration needs to be maintained in the bioreactor to achieve nitrification? When the NR value is high, meaning a higher population of nitrification bacteria, the plant can afford to use a lower biomass concentration in the bioreactor to achieve nitrification, whereas a lower NR calls for maintaining higher biomass concentration in the bioreactor.

6) The NR measurement also allows the operator of the wastewater treatment plant to estimate how much wastewater influent the plant can treat with the existing facility, therefore planning for plant expansion or modification.

Denitrification rate, DR, can be used in the monitoring and control of biological denitrification within the wastewater treatment process. When DR is measured on a real time basis, the information can answer the following:

1) What is the capacity of denitrification in the bioreactor? Based on the measured DR value, information on the nitrate loading to the anoxic zone, hydraulic retention time in the anoxic zone, and the desired degree of denitrification, one can estimate how much wastewater influent the plant can treat.

2) What is the optimal internal recycle rate to the anoxic zone? The nitrate loading to the anoxic zone fundamentally comes from the internal recycle of the nitrified mixed liquor at the end of the aerobic zone of a bioreactor, referring to FIG. 1 for the location of denitrification internal recycle. Knowing the DR allows accurate control of the internal recycle, thus achieving full utilization of the anoxic zone and avoiding wasting pumping energy from over-recycling.

3) Is there any factor limiting the achievement of optimal denitrification? The DR measurement allows the evaluation of denitrification activity in terms of carbonaceous nutrient and nitrate loading. A lower DR indicates an endogenous denitrification, as carbonaceous nutrient is limited. Increased carbonaceous nutrient loading enhances the denitrification process. A higher DR, on the other hand, predicts an active denitrification process. Increasing the internal recycle improves the total nitrogen removal from the wastewater stream.

The invention may be applied to any kind of microbial process including, but not limited to, wastewater purification (municipal, industrial and the like), pharmaceutical/biotechnology production, brewing, fermentation or any other process involving pure or mixed populations of micro organisms.

Although this invention has been described with reference to specific forms of apparatus and method steps, it will be apparent to one of ordinary skill in the art that various equivalents may be substituted, the sequence of steps may be varied, and certain steps may be used independently of others. Further, various other control steps may be included, all without departing from the spirit and scope of the invention defined in the appended claims.

What is claimed is:

1. A method of measuring $NO_x$ in a liquid sample comprising:

a) isolating a liquid sample;

b) adjusting the pH and/or ionic strength of said sample at time $t_0$;

c) recording a first value $mV_1$ present in said sample with an $NO_x$ selective probe at a first predetermined time $t_1$;

d) recording a second value $mV_2$ present in said sample after a second predetermined time $t_2$;

e) determining $NO_x$ concentrations in said sample at each of said predetermined times $t_1$ and $t_2$ according to the following formula:

$$[NO_x] = 10^{a \cdot mVx + b}$$

wherein a and b are linear coefficients of the $NO_x$ probe;

f) determining changes in $NO_x$ in said sample according to the following formula:

$$\Delta[NO_x] = [NO_x]_2 - [NO_x]_1;$$

and wherein $[NO_x]_1$ is the concentration of $NO_x$ at the predetermined time $t_1$ and $[NO_x]_2$ is the concentration of $NO_x$ at the predetermined time $t_2$;

g) determninig the $NO_x$ concentration of the sample according to the following formula:

$$[NO_x]_0 = [NO_x]_1 - \frac{\Delta[NO_x]}{\Delta t} \cdot (t_1 - t_0),$$

wherein $\Delta t$ is $t_2 - t_1$.

2. The method defined in claim 1 further comprising repeating steps a)–g).

3. The method defined in claim 1 further comprising periodically calibrating said $NO_x$ selective probe.

* * * * *